United States Patent [19]
Barker

[11] Patent Number: 5,201,320
[45] Date of Patent: Apr. 13, 1993

[54] BLOOD PRESSURE MEASURING DEVICE
[75] Inventor: Kent R. Barker, Eagan, Minn.
[73] Assignee: Prevention Sciences Incorporated, Eagan, Minn.
[21] Appl. No.: 714,654
[22] Filed: Jun. 13, 1991
[51] Int. Cl.⁵ .......................................... A61B 5/0225
[52] U.S. Cl. ................... 128/680; 128/684; 128/677; 128/672
[58] Field of Search ............... 128/680, 681, 684, 666, 128/677, 672, 667, 900

[56] References Cited

U.S. PATENT DOCUMENTS

| | | | |
|---|---|---|---|
| 4,005,701 | 2/1977 | Aisenberg et al. | 128/680 |
| 4,262,675 | 4/1981 | Kubo et al. | 128/680 |
| 4,417,586 | 11/1983 | Jewett | 128/680 |
| 4,427,013 | 1/1984 | Nunn et al. | 128/681 |
| 4,592,365 | 6/1986 | Georgi | 128/680 |
| 4,706,684 | 11/1987 | Sorensen et al. | 128/677 |
| 4,716,906 | 1/1988 | Ruff | 128/686 |
| 4,727,885 | 3/1988 | Ruff | 128/686 |
| 4,729,383 | 3/1988 | Susi | 128/681 |
| 4,745,924 | 5/1988 | Ruff | 238/686 |
| 4,754,761 | 7/1988 | Ramsey et al. | 128/683 |
| 4,776,344 | 10/1988 | Shirasaki et al. | 128/681 |
| 4,777,959 | 10/1988 | Wallach et al. | 128/677 |
| 4,779,626 | 10/1988 | Peel et al. | 128/675 |
| 4,785,820 | 11/1988 | Brooks | 128/681 |
| 4,796,184 | 1/1989 | Bahr et al. | 364/413.03 |
| 4,799,492 | 1/1989 | Nelson | 128/672 |
| 4,807,638 | 2/1989 | Sramek | 128/672 |
| 4,830,019 | 5/1989 | Shirasaki et al. | 128/681 |
| 4,840,181 | 6/1989 | Yamaguchi | 128/680 |
| 4,860,761 | 8/1989 | Yamasawa et al. | 128/686 |
| 4,869,261 | 9/1989 | Penaz | 128/667 |
| 4,870,973 | 10/1989 | Ueno | 128/680 |
| 4,872,461 | 10/1989 | Miyawaki | 128/681 |
| 4,889,133 | 12/1989 | Nelson et al. | 128/681 |
| 5,103,830 | 4/1992 | Shinomiya | 128/680 |

FOREIGN PATENT DOCUMENTS

84/01499  4/1984  World Int. Prop. O. .......... 128/680

Primary Examiner—Lee S. Cohen
Assistant Examiner—Brian Casler
Attorney, Agent, or Firm—Kinney & Lange

[57] ABSTRACT

In combination with a conventional sphygmomanometer, a solenoid, an air release valve connected to the solenoid for the release of air from the cuff bladder of the sphygmomanometer, a pressure transducer for determining air pressure in the cuff bladder and generating a pressure data signal, a data processing unit for monitoring and recording pressure signal readings and controlling the solenoid, and a signaling unit used to designate when to record a pressure signal are provided.

7 Claims, 9 Drawing Sheets

BLOOD PRESSURE MEASURING DEVICE

FIELD OF THE INVENTION

The invention relates to sphygmomanometers, and particularly to partial automation of sphygmomanometer operation.

BACKGROUND OF THE INVENTION

The heart maintains blood flow to the tissues of the body by its pumping action. Blood courses outward to all parts of the body through an arterial tree. The arterial tree has as its trunk the aorta, which receives blood as it is expelled from the heart. Major branches include the carotid arteries leading to the head and the brachial artery leading to each arm. Numerous smaller arteries and capillaries reach essentially all parts of the body. Blood pressure is pressure in the arterial system, i.e. pressure in the distribution part of the circulatory system.

Blood pressure varies with the beating of the heart. It peaks during systole, the contraction of the heart's left ventricle, during which blood is ejected into the aorta. The peak pressure is systolic pressure. As the left ventricle relaxes during diastole, blood pressure gradually falls to a minimum. The minimum pressure is the diastolic pressure. The ejection of blood into the aorta gives rise to the pulse felt in arteries.

Medical diagnostics relies heavily on measurement of blood pressure as an indication of cardiovascular function, cardiovascular morbidity and mortality. Absolute accuracy in measurement requires invasive techniques, i.e. the insertion into an artery of a needle or catheter. However, indirect and "noninvasive" measurement techniques are typically used. Lower cost and greater convenience and comfort for the patient dictate indirect measurement. The term "indirect" means that the measurement is not of actual pressure. A technique is "noninvasive" in that the body is not actually penetrated.

One method of indirect blood pressure measurement is the occluding-cuff auscultatory technique. An occluding-cuff is an unyielding cuff which is positioned around the arm of a patient for the test. Properly positioned and closed, the cuff positions and retains an air bladder over the brachial artery. The bladder occludes the brachial artery upon sufficient inflation. Auscultation is the act of listening. In medicine the term auscultation refers to the diagnostic monitoring of sounds made by internal body parts or organs. An example of auscultation is the use of a stethoscope to listen to heart or lung action. In the "occluding-cuff auscultatory technique" sounds are produced in the brachial artery by the intermittent flow of blood. Blood flow is intermittent as a result of pressure applied to the artery by the bladder. The diagnostically significant sounds are called Korotkoff sounds. The various Korotkoff sounds signify certain things to a trained user. The user takes pressure readings of bladder pressure as the various types of Korotkoff sounds are heard.

Korotkoff sounds associated with the beginning of intermittent blood flow through an artery and occurring just before the disappearance of all sound are the most significant. Phase I sounds occur at the highest pressure, where blood flow can just occur at the highest blood pressure. Phase V sounds occur at the lowest pressures at which blood flow can be interrupted at all. The measurements are commonly taken on the brachial artery to standardize readings. The first pressure is peak arterial pressure, i.e. systolic pressure. The lowest pressures are minimum arterial pressure, i.e. diastolic pressure.

Medical practitioners employ two familiar instruments in practicing this technique. One instrument is the common stethoscope, which is used to amplify the Korotkoff sounds. The second instrument is called a sphygmomanometer. The sphygmomanometer includes the cuff and bladder described above, a bulb for pressurizing the bladder with air, a valve for releasing air from the bladder and some type of pressure indicator. Higher quality sphygmomanometers have a mercury containing column as a pressure indicator. The column is graduated to indicate pressure in the bladder.

In practicing the technique, the medical practitioner applies the cuff around the upper arm of a patient and inflates the bladder to occlude the brachial artery. She then places the sound gathering end of the stethoscope over the brachial artery below the cuff. She releases air from the bladder by a manually actuated valve and notes the pressures at which valid Korotkoff sounds appear and again disappear.

Researchers have focused much effort relating to blood pressure measurement techniques on automating the detection of Korotkoff sounds. For example, U.S. Pat. No. 4,592,365 relates to an "Electronic Sphygmomanometer". The patent discloses a device for the automatic detection, verification and evaluation of Korotkoff sounds. Waveform analysis provides the basis for achieving these functions. Transducers provide cuff flex sensing relating to pressure waves, upstream and downstream microphones for detecting Korotkoff sounds, and a pressure transducer measuring the pressure in the sphygmomanometer. Korotkoff sound signals and blood pressure pulses, which are precursors to true Korotkoff sounds, are obtained from the separate transducers. Separate channels are provided for the sound and pressure wave data. Separate waveform analysis of the two signals can then be provided. Korotkoff sounds are verified dependent upon signal slope characteristics and proper phase relationship to the pressure pulse waveform. Upon Korotkoff sound verification, the pressure transducer reading is automatically noted.

Implicit in the focus on automation of the steps of blood pressure measurement is lack of confidence in the quality of human observation. There is some basis for such lack of confidence. In a front page article reported in the Saint Paul Pioneer Press on 9 Jan. 1991, studies have indicated wide spread failure to conform blood pressure measurement procedures with those recommended by the American Heart Association. The recommendations appear in the pamphlet "Recommendations for Human Blood Pressure Determination by Sphygmomanometers", published by the American Heart Association, 7320 Greenville Avenue, Dallas, Tex. 75231. For example, only about 20% of the practitioners take the recommended two readings and average those readings. Of those practitioners who take two readings, fewer still wait the recommended 30 seconds between readings. Some practitioners exhibit what is known as terminal digit preference. While these and other factors suggest unreliability in human observation, these causes do not necessarily mean that the human is not the best arbiter of the subtle variations which characterize Korotkoff sounds.

The causes of the poor performance by many practitioners included inconsistent or incomplete training and laziness. The occluding-cuff auscultatory technique is complex in terms of hand, eye and ear coordination. The practitioner must watch changing pressure indications in a column of mercury, listen for Korotkoff sounds and control the rate of deflation of the bladder. The user watches the pressure indications both to control the rate of deflation and to note the pressures at which the appropriate Korotkoff sounds occur. Both systematic and random error can result from this arrangement. Error may be induced by the number of simultaneous tasks the practitioner must do.

SUMMARY OF THE INVENTION

The conclusion drawn from the occasion of human error in blood pressure measurement, i.e. that the human must be removed from as much of the process as possible, is not a logical necessity. It is this Inventors's conclusion that automation of those aspects of the operation of the sphygmomanometer which unnecessarily burden the operator should improve human performance, particularly in the art of detecting and qualifying valid Korotkoff sounds. Thus the invention is directed to simplifying the method and to guiding the practitioner to use of proper technique. The invention provides automatic control in reduction in bladder pressure. A further improvement relates to the manner of recording systolic and diastolic blood pressure. The invention provides recording of pressure readings automatically in response to depression of buttons of a control system. The need to note and remember pressures occurring at the onset of the appropriate aural condition is eliminated. Averaging of two readings occurs automatically, reducing the work burden on the medical practitioner. Medical practitioners are left free to focus on what they do best, which is the interpretation of the various sounds heard from the stethoscope. The operator detects and distinguishes between various sounds to determine which are valid Korotkoff sounds and responds to the valid sounds with a simple hand movements. Virtually all remaining functions are automated.

The invention comprises, in combination with a conventional sphygmomanometer, a solenoid, an air release valve connected to the solenoid for releasing air from the cuff bladder of the sphygmomanometer, a pressure transducer for determining air pressure in the cuff bladder and generating a pressure data signal, a data processing unit for monitoring and recording pressure signal readings and controlling the solenoid, and a manual signaling unit used to designate when to record a pressure signal.

DETAILED DESCRIPTION OF THE PREFERRED EMBODIMENT

Figure 1:
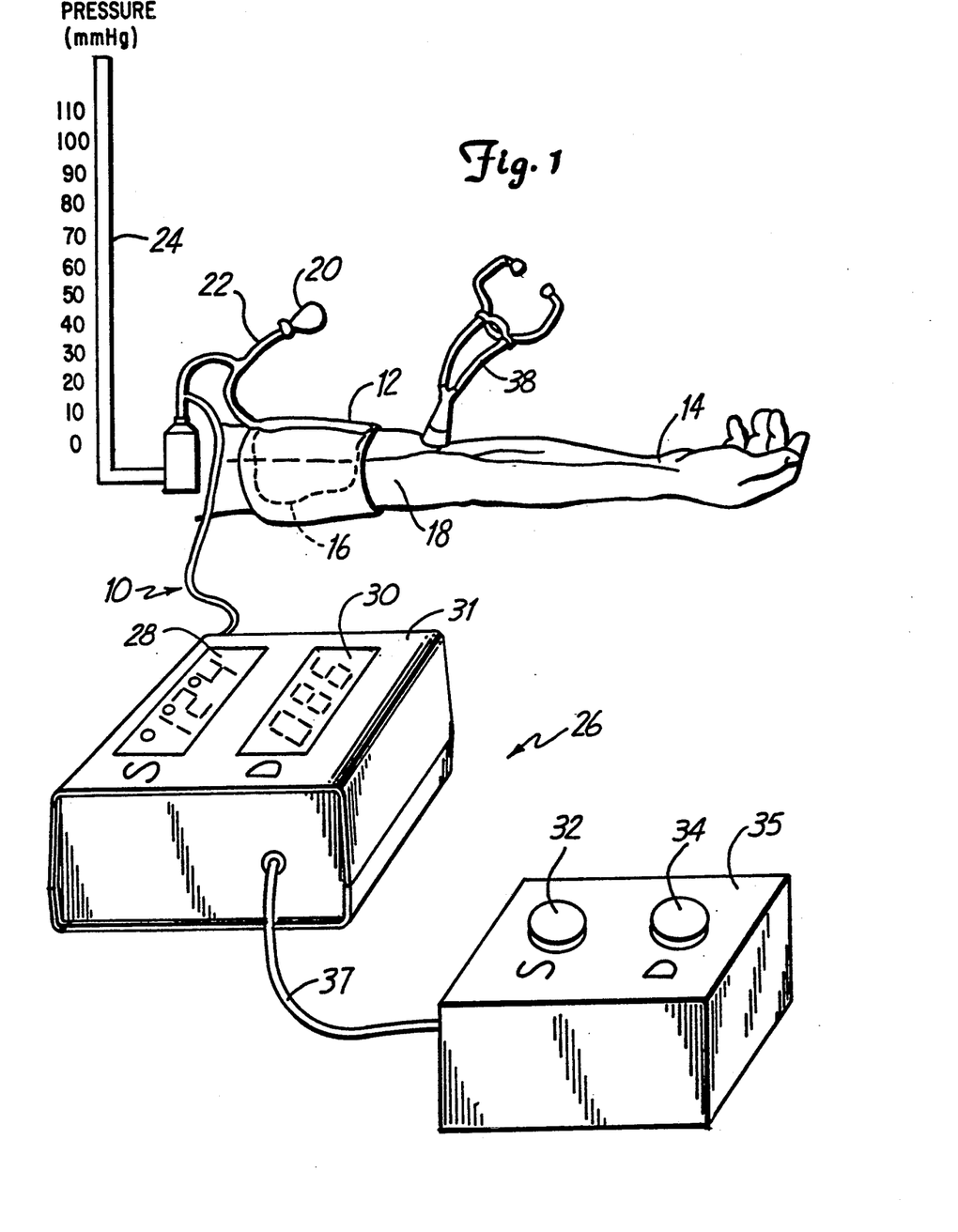
FIG. 1 is a perspective, exterior view of the apparatus of the present invention.

FIG. 1 illustrates a sphygmomanometer 10. Sphygmomanometer 10 provides a mechanism for the controlled occlusion of brachial artery 18 in arm 14 and the determination of the pressure required to obtain a specific degree of occlusion. Sphygmomanometer 10 includes a nonyielding arm cuff 12 wrapped around arm 14. Cuff 12 typically includes cooperating fastening tape or hooks and is firmly fitted to arm 14. Arm cuff 12 has an inflatable air bladder 16, partially wrapped around arm 14 and positioned over brachial artery 18. A pressurization bulb 20 is connected to bladder 16 by a tube system 22 and may be grasped by a medical practitioner to pressurize the bladder. Upon pressurization bladder 16 expands, pushing against cuff 12 and compressing arm 14. Upon pressurization of bladder 16, brachial artery 18 will be occluded unless the instant blood pressure exceeds pressure applied to the arm. For the appropriate pressures in bladder 16, brachial artery 18 is occluded save at peak blood pressure (i.e. systolic blood pressure), or occluded only at or around the minimum blood pressure (i.e. diastolic pressure).

Bladder air pressure is equated with blood pressure. Accordingly, instruments provide a reading of any foreseeable pressure in bladder 16. Two such instruments may be provided. A mercury column manometer 24 is connected to bladder 16 by tube system 22, and a second instrument is incorporated in a display and control system 26. However, in the alternative, only the display control system 26 may be used. Display and control system 26 includes a pressure transducer and associated electronic control circuitry for operation of measurement systolic display 28 and diastolic display 30 forming part of a first unit 31. (See FIG. 2). The transducer is connected by tube system 22 to bladder 16. In the present invention, the primary use of mercury column manometer 24 is the calibration of the pressure transducer control circuitry of display and control system 26.

Display and control system 26 presents its user with control arrangements of minimal complexity. Light Emitting Diode ("LED") displays 28 and 30 give pressure readings and certain other information in accordance with a strict protocol. Buttons or switches 32 and 34 (forming part of a "mouse"-like second unit 35 of the system 26 which is coupled to the first unit 31 by communication line 37) are pressed upon detection by the user of the Korotkoff sounds associated with systolic and diastolic pressures, respectively. In certain operating modes the simultaneous depression of both switches 32 and 34 initiates certain operations by system 26 described below.

Sphygmomanometer 10 has an ON mode and an OFF mode. The OFF mode is a power conserving mode during which display 78 is unpowered. The device is actually "on" as long as a good battery is installed. During the OFF mode, cuff 12 is sensed for closure once a second. ON/OFF status is controlled by strapping cuff 12 onto the arm of a patient. Closure of cuff 12 puts sphygmomanometer 10 into its ON mode. In the ON mode display 78 is activated and microprocessor 50 (see FIG. 2) begins execution of a preprogrammed subroutine at step 100 (see FIGS. 3-9).

Korotkoff sounds are monitored by a medical practitioner using a stethoscope 38. By positioning stethoscope 38 over brachial artery 18 below cuff 12 and listening during the release of pressure from bladder 16, the beginning of the clear tapping sounds associated with systolic pressure (the so-called Phase I sounds) and the final disappearance of all sound (the so-called Phase V sounds) associated with diastolic pressure levels can be monitored.

Figure 2:
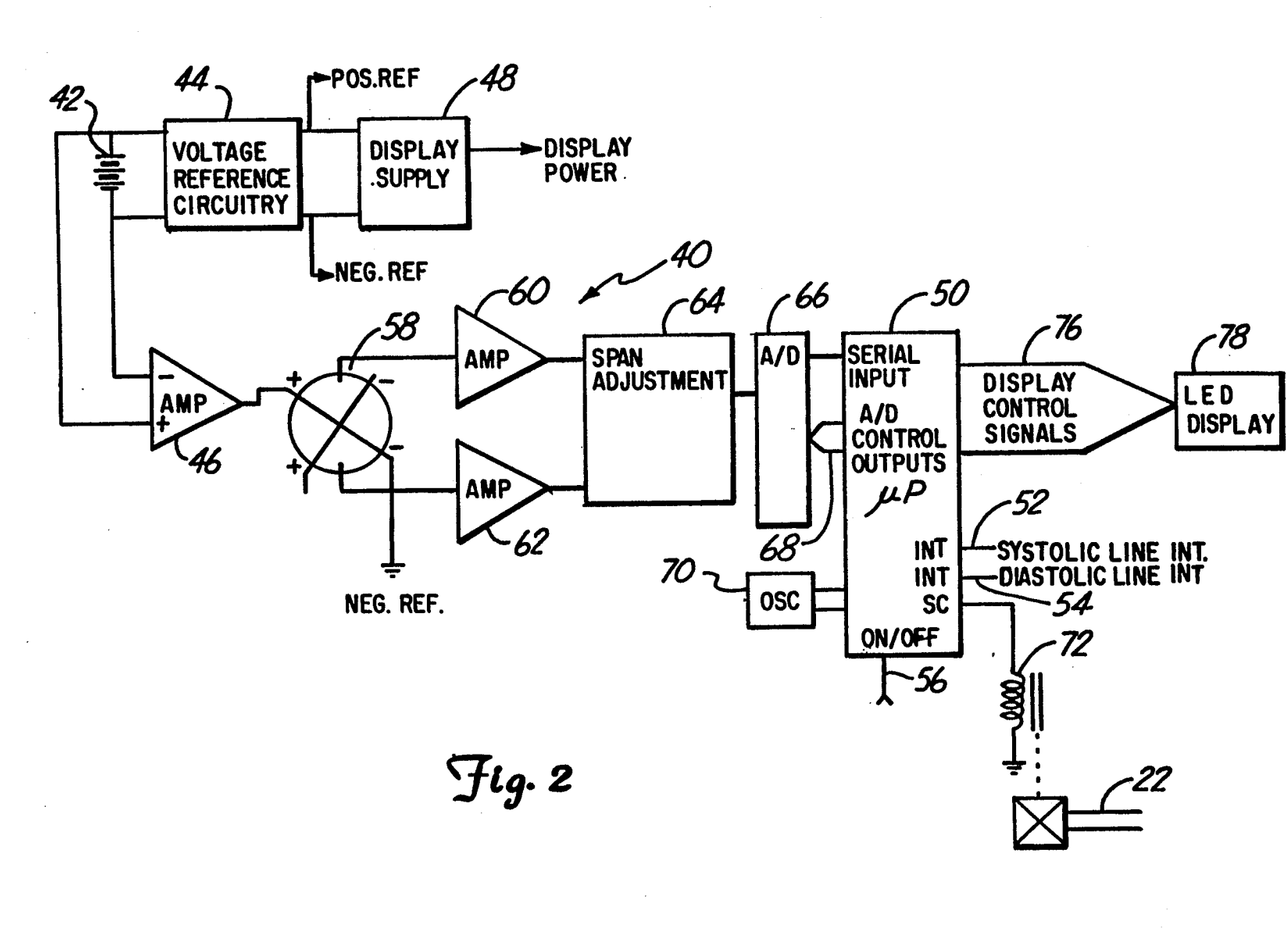
FIG. 2 is a block diagram of an electrical circuit suitable for control of the functions of the apparatus of the present invention.

FIG. 2 illustrates a block-diagram schematic of display and control system 26. The heart of control circuitry 40 is a microprocessor 50. Microprocessor 50 is preferably a Motorola MC68HC705C8 type microprocessor. The remainder of the circuitry is devoted to powering microprocessor 50 or other supplementary functions, such as generating inputs to microprocessor 50, displaying results of microprocessor 50 operations, or carrying microprocessor 50 external commands.

Power comes from a nickel-cadmium battery 42. Battery 42 supplies power to voltage reference circuitry 44. In turn, voltage reference circuitry 44 provides voltages at regulated levels to various components of control circuitry 40 as required for their normal operation. In particular, display power circuit 48 takes its inputs directly from the voltage reference circuitry 44.

Inputs to microprocessor 50 are of two types, interrupt signals and pressure readings. External interrupts are generated by a user depressing one or both of the signalling buttons 32, 34. Buttons 32 and 34 control a systolic line interrupt 52 and a diastolic line interrupt 54. An ON/OFF signal line 56 allows microprocessor 50 to sense closure status of cuff 12. A line interrupt signal causes certain predetermined processes to be executed by microprocessor 50. The process steps are described in greater detail below. Under normal circumstances, receipt of an interrupt signal results in the retaining the current pressure reading in an appropriate memory location. Presence of both interrupt signals results in execution of other processing steps.

Depression of the systolic or diastolic button 32 and 34 must be maintained for a minimum time period before microprocessor 50 will respond positively to the presence of the resultant interrupt signals on lines 52 or 54. Basically, the initial response to an interrupt signal is execution of a "DEBOUNCE" routine. The routine counts the number of consecutive clock periods where an interrupt signal appears. If neither line is high for the requisite number of periods, the interrupt is ineffective.

A differential pressure transducer 58 is the source of the pressure signals upon which microprocessor 50 operates. Transducer 58 is energized by an amplifier 46, which buffers the terminals of battery 42 from the transducer. Pressure changes in bladder 16 effect the electrical resistance characteristics of transducer 58, effecting in turn output signals from the transducer. Amplifiers 60 and 62 take the output signals of transducer 58 as inputs and apply their outputs to a span adjustment circuit 64. Span adjustment circuit 64 imposes a maximum output range, for application to an analog to digital converter 66.

Microprocessor 50 operates on digital inputs, i.e. inputs of discrete values. The output of a transducer 58 is continuous or analog. Analog to digital converter converts the output signals of span adjustment circuit 64 within certain ranges to certain predetermined discrete digital values. Analog to digital converter 66 is under the control of microprocessor 50 via bus 68. Control inputs to analog to digital converter 66 include the clock signal. Sampling occurs about each one-half second, which is a preferred period for the measurement cycle. Analog to digital converter 50 passes the digital representations of pressure signals to microprocessor 50 serially. Analog to digital conversion uses a dual slope algorithm.

Microprocessors operate sequentially under control of a clock signal. A local crystal controlled oscillator 70 provides the clock signal for microprocessor 50. The clock signal is a 200 kilohertz signal.

Microprocessor 50 controls deflation of bladder 16. Microprocessor 50 generates solenoid control output signals, which are applied to a solenoid 72. Solenoid 72 in turn opens and closes a valve 74 connected to tubing 22. Upon opening, valve 74 allows air under pressure in bladder 16 to escape.

Microprocessor 50 relays the systolic and diastolic pressure measurements to the medical practitioner for interpretation. Display 78, which includes systolic and diastolic displays 28 and 30, provides this function. A display, control bus 76 connected between microprocessor 50 and display 78 transmits control signals from the microprocessor to the display FIGS. 3-9 are flow charts of programming for microprocessor 50. Features of the operation of sphygmomanometer 10 are explained with reference to its programming. The programming of sphygmomanometer 10 provides for taking two sets of blood pressure measurements and for their averaging. The operating programming further assures that two sets of measurements are properly spaced in time, i.e. the thirty seconds. A palpation mode is provided for initial estimation of systolic pressure. This is used to determine initial pressurization.

Figure 3:
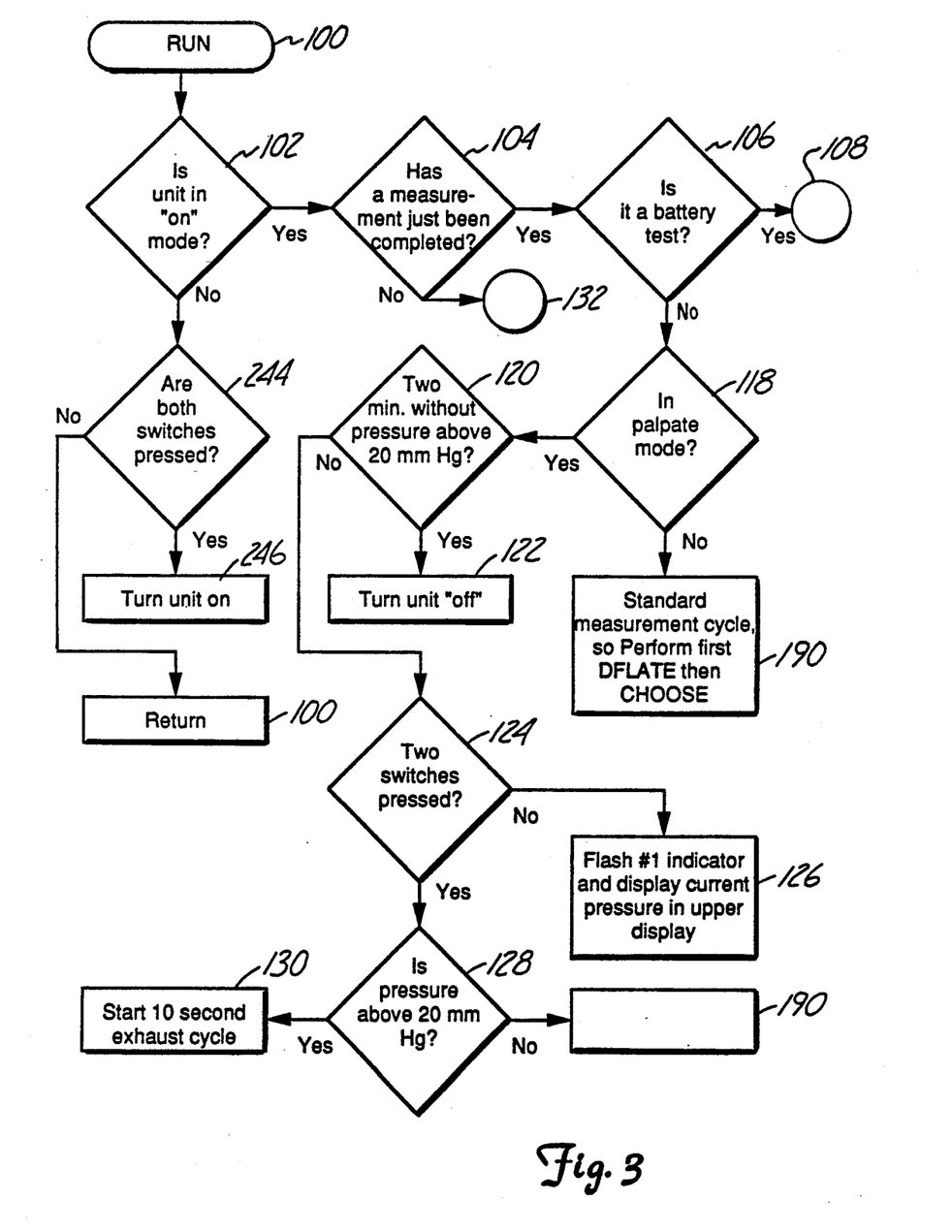
FIGS. 3-9 are flow charts of routines executed by the microprocessor of the electrical circuit of FIG. 2.

Step 100 labeled "RUN", is either an entry or reentry point for the "RUN" module executed on microprocessor 50. As an entry point it is the default step upon power up. As a reentry point it is a step commonly returned to upon completion of certain subprograms or subroutines.

Execution of step 102 follows step 100. Step 102 is labeled "IS UNIT IN ON MODE?" and is a decision branch in the programming. A positive answer leads to step 104, a further decision branch in the programming labeled "HAS A MEASUREMENT JUST BEEN COMPLETED?". A positive answer leads to step 106, another decision branch labeled "IS IT A BATTERY TEST?". A positive response, causes a battery test subroutine which begins at step 108 shown separately in detail in FIG. 6.

Step 108 (FIG. 6) is labeled "IS BATTERY VOLTAGE BELOW 8 VOLTS?" and is another decision branch in the programming. A battery voltage of greater than 8 volts results in program execution to move to step 110 which indicates that the system 26 is operational and the program routine returns to step 100 (FIG. 3). If the battery voltage is below 8 volts, program execution moves to step 112, a decision branch labeled "IS BATTERY VOLTAGE BELOW 7.5 VOLTS?". A battery voltage of greater than 7.5 volts moves program execution to step 114, which sets the displays 28 and 30 flashing as a low charge warning. If the battery voltage is less than 7.5 volts, program execution moves to step 116 which shuts down the microprocessor 50.

Returning to step 106, in absence of a battery test, program execution moves to step 118, a decision branch labeled "IN PALPATE MODE?". An initial estimation of systolic pressure is made for operation in the palpate mode. The estimated systolic pressure, plus 30 mm Hg of pressure, which provide a palpate mode pressure estimation, provides a convenient initial pressurization of cuff bladder 16 to begin blood pressure measurement. Any comfortable cuff bladder pressure which assures occlusion of the brachial artery is acceptable. Since a systolic blood pressure lower than 10 mm Hg in a living person is unknown, any reasonably conceivable palpate mode estimation must exceed 40 mm Hg of pressure.

Entry into the palpate mode is automatic upon turning system 26 on or upon completion of the 20 second display of the average systolic and diastolic blood pressure measurements. Entry into the palpate mode causes program execution to move to step 120, a decision branch labeled "TWO MINUTES WITHOUT PRESSURE ABOVE 20 mm Hg?". A positive response moves program execution to step 122 which turns the system 26 off. A negative response moves program routine to step 124. If cuff pressure is above 20 mm Hg, and the buttons 32 and 34 are not depressed, the current cuff pressure is displayed in display 28 as indicated in step 126. If the buttons 32 and 34 are both depressed simultaneously, the program routine moves to step 128. Step 128 is a decision branch labeled "IS PRESSURE ABOVE 20 mm Hg?". A cuff pressure above 20 mm Hg initiates exhaust and the start of the 10 second timer indicated in step 130.

Returning to step 104, a negative response leads to step 132, a decision branch labeled "IS THIS A PALPATE MODE TIMER?". Absent running of the palpate mode timer and measurement timers 1 and 2 (steps 134 and 136) and upon completion of the 20 second timer (step 138), program execution moves back to palpate mode step 118. If the 20 second timer is running, program execution defaults to the decrement timer indicated in step 140. Returning to step 132 (FIG. 4), if this is the palpate mode timer and the timer is not complete (step 142), program execution defaults to the decrement timer indicated in step 144.

Figure 4:
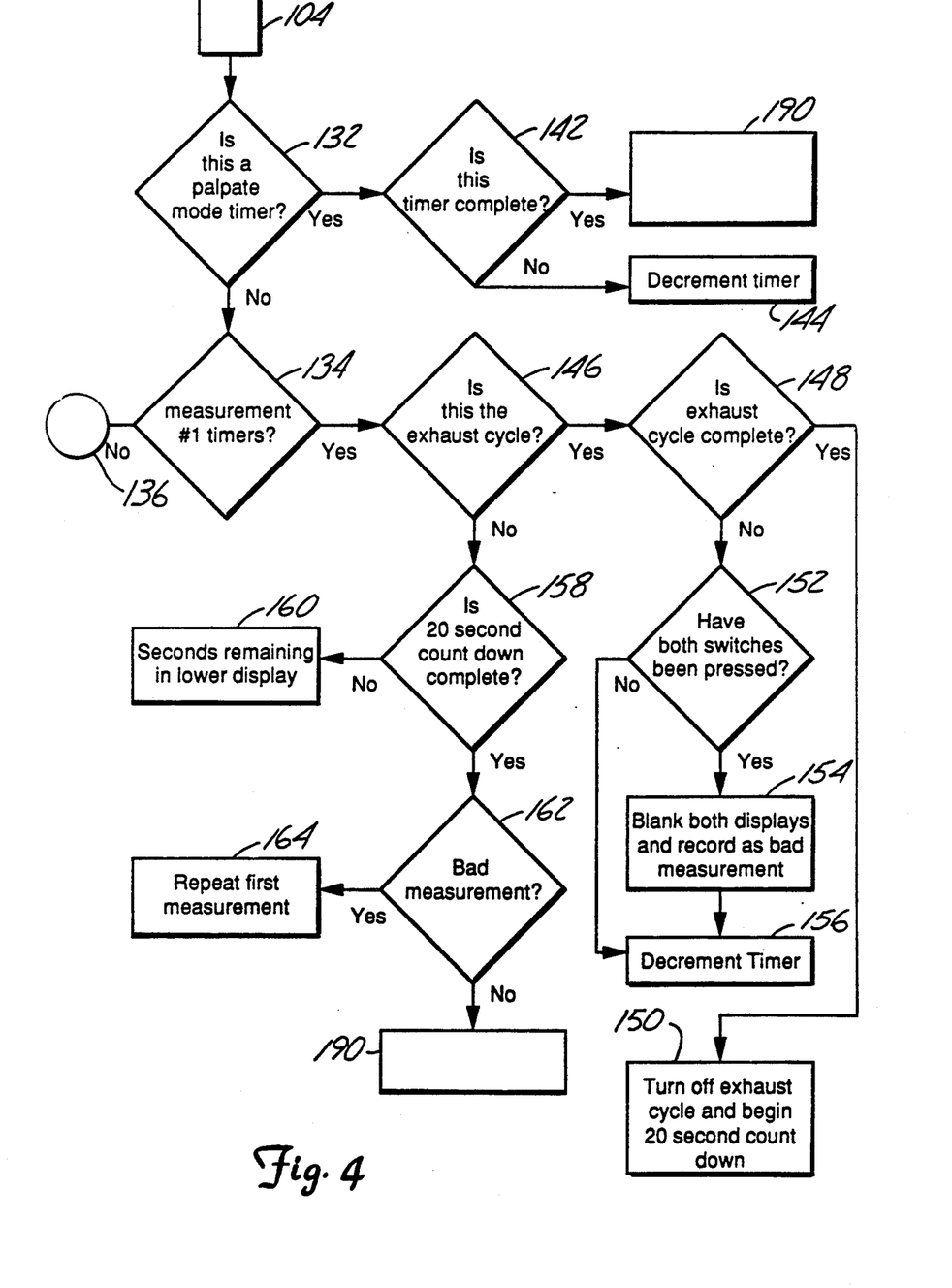

A positive response at step 134 moves program execution to step 146. Step 146 is a decision branch labeled "IS THIS THE EXHAUST CYCLE?". A positive response at step 146 moves program execution to step 148 a decision branch labeled "IS EXHAUST CYCLE COMPLETE?". If the exhaust cycle is complete, program execution moves to step 150 wherein the exhaust cycle is terminated and the 20 second timer is initiated. An incomplete exhaust cycle moves program execution to step 152. Depressing both buttons 32 and 34 simultaneously blanks displays 28 and 30 (step 154) to indicate a bad measurement before decrementing the timer (step 156). If the buttons 32 and 34 have not both been depressed, program execution immediately causes decrementing of the timer (step 156).

Returning to step 146, if this is not the exhaust cycle and the 20 second count down is running (step 158), display 28 merely displays the time remaining (step 160). If the 20 second countdown is complete and the measurement is bad (step 162), the program executes the first systolic/diastolic measurement (step 164).

Figure 5:
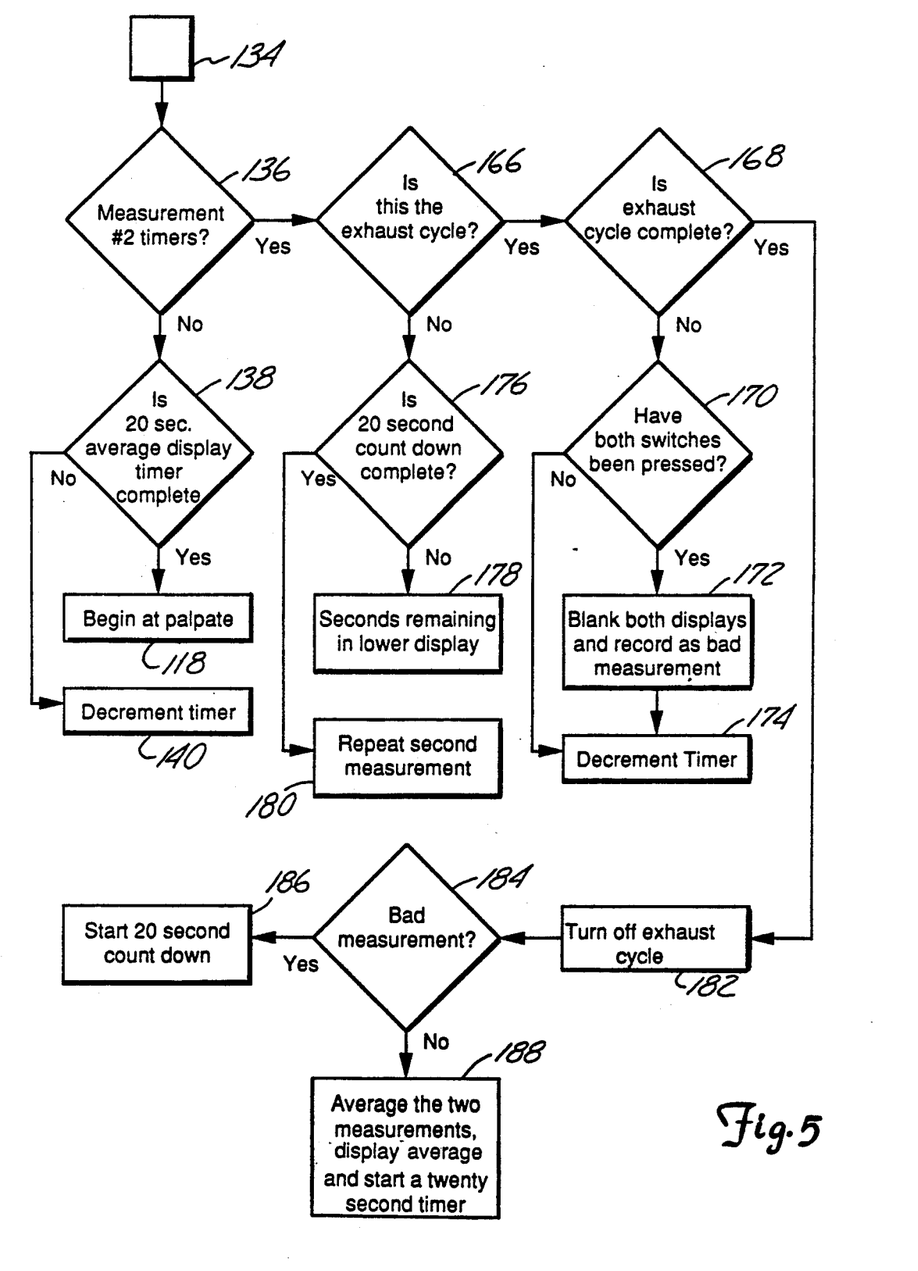
Figure 6:
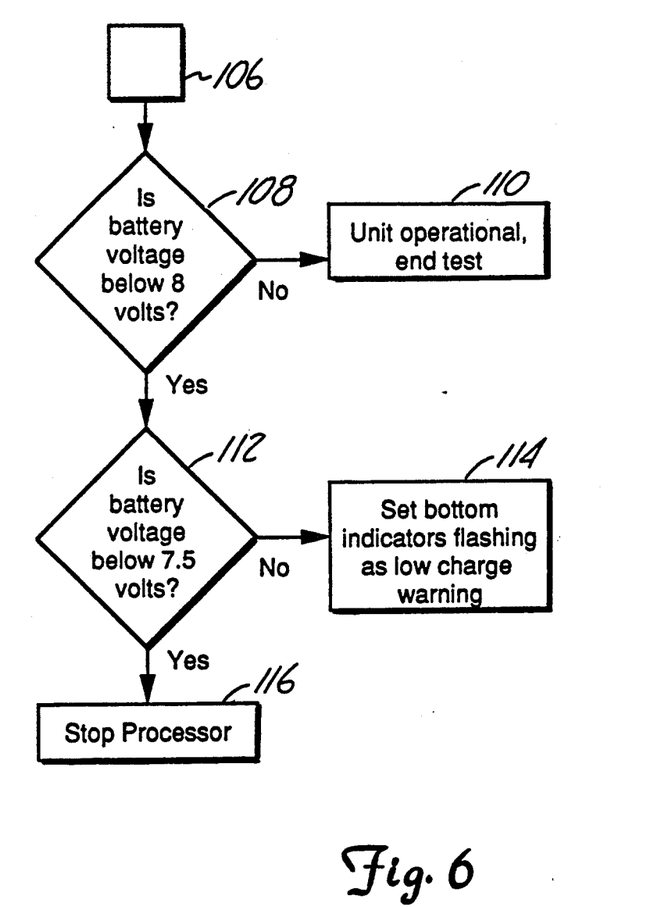
Figure 7:
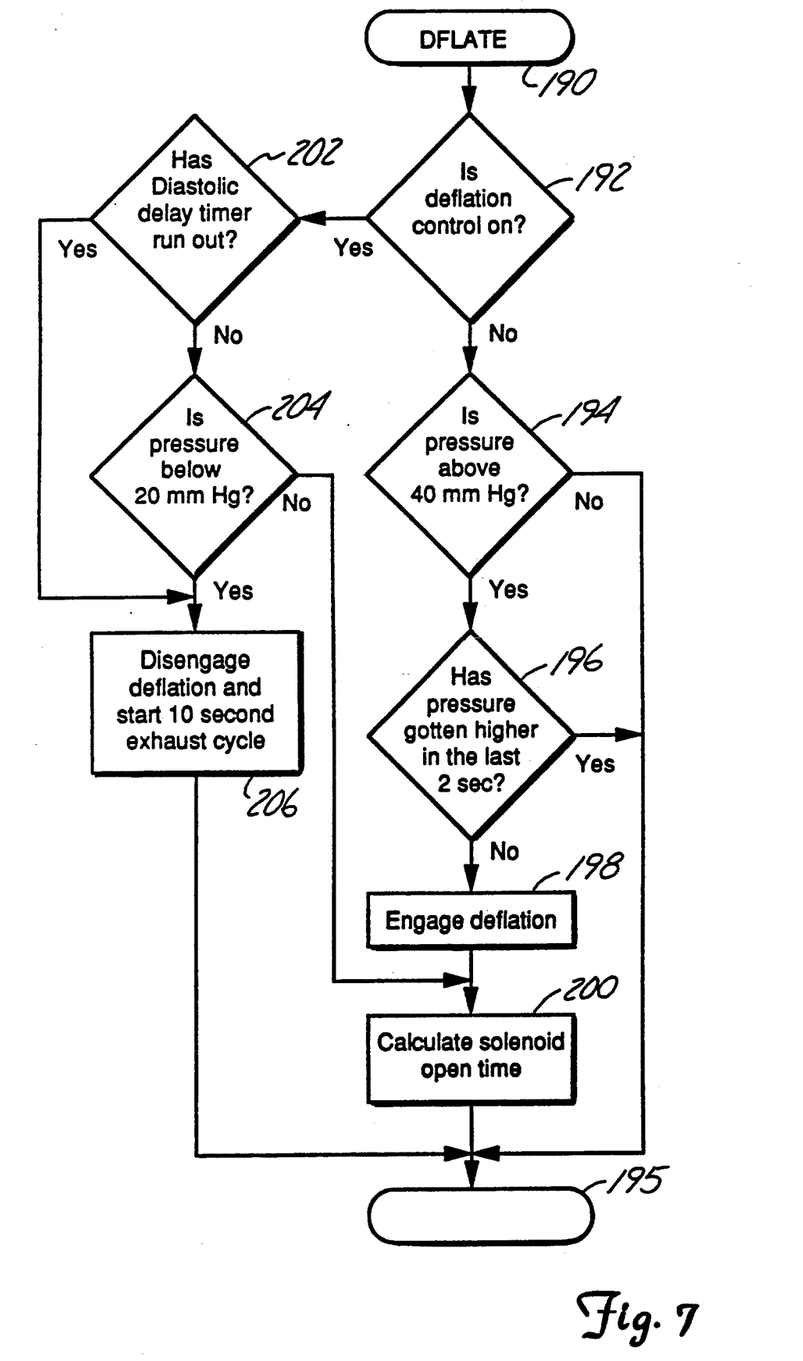

Returning to step 136, a positive response at step 136 moves program execution to step 166 (FIG. 5). Step 166 is a decision branch labeled "IS THIS THE EXHAUST CYCLE?". A positive response at step 166 moves program execution to step 168 a decision branch labeled "IS EXHAUST CYCLE COMPLETE?". A negative response at step 168 moves program execution through steps 170, 172 and 174 that are identical to steps 152, 154 and 156 respectively.

Returning to step 166, if this is not the exhaust cycle and the 20 second count down is running (step 176), display 28 merely displays the time remaining (step 178). If the 20 second count down is complete, the second measurement is repeated (step 180). Returning to step 168, a positive response turns off the exhaust cycle (step 182) and program execution moves to step 184. Step 184 is a decision branch labeled "BAD MEASUREMENT?". If the second systolic/diastolic pressure measurement is bad the 20 second countdown is initiated (step 186), if the second systolic/diastolic pressure measurement is good, the two measurements are averaged and displayed and the 20 second timer is initiated (step 188).

Returning to step 118, a negative response moves program execution into the "DEFLATE" module executed on microprocessor 50. Step 190 labeled "DEFLATE" (FIG. 7), is either an entry or reentry point for the "DEFLATE" module. Execution of step 192 follows step 190. Step 192 is labeled "IS DEFLATION CONTROL ON?" and is a decision branch in the programming. A negative response moves program execution to step 194 which is a further decision branch labeled "IS PRESSURE ABOVE 40 mm Hg?". If the systolic pressure is below 40 mm Hg, program execution moves to step 195. If the systolic pressure is above 40 mm Hg, program execution moves to step 196 which is a further decision branch labeled "HAS PRESSURE GOTTEN HIGHER IN THE LAST 2 SECONDS?". If the systolic pressure has gotten higher in the last 2 seconds, program execution moves to step 195. If the systolic pressure has not gotten higher, deflation is engaged (step 198), the solenoid open time is calculated (step 200) and program execution moves to step 195.

Returning to step 192 (FIG. 7), a positive response moves program execution to step 202. Step 202 is a further decision branch labeled "HAS DIASTOLIC DELAY TIMER RUN OUT?". If the diastolic delay timer has not run out, program execution moves to step 204, which is a further decision branch labeled "IS PRESSURE BELOW 20 mm Hg?". If systolic pressure is above 20 mm Hg, program execution moves to step 200 and then to step 195. A positive response at either step 202 or step 204 moves program execution to step 206 which causes disengagement of deflation, initiation of the 10 second exhaust cycle and a return to step 195.

Step 195 labeled "CHOOSE" (FIG. 8), is either an entry or reentry point for the "CHOOSE" module executed on microprocessor 50. Execution of step 208 follows step 195. Step 208 is labeled "IS SYSTOLIC SELECTED?" and is a decision branch in the programming. A negative response moves program execution to step 210, which is a further decision branch labeled "IS THIS THE FIRST MEASUREMENT?". If it is the first measurement, current measured blood pressure is stored in Systolic area #1 (step 212).

Figure 8:
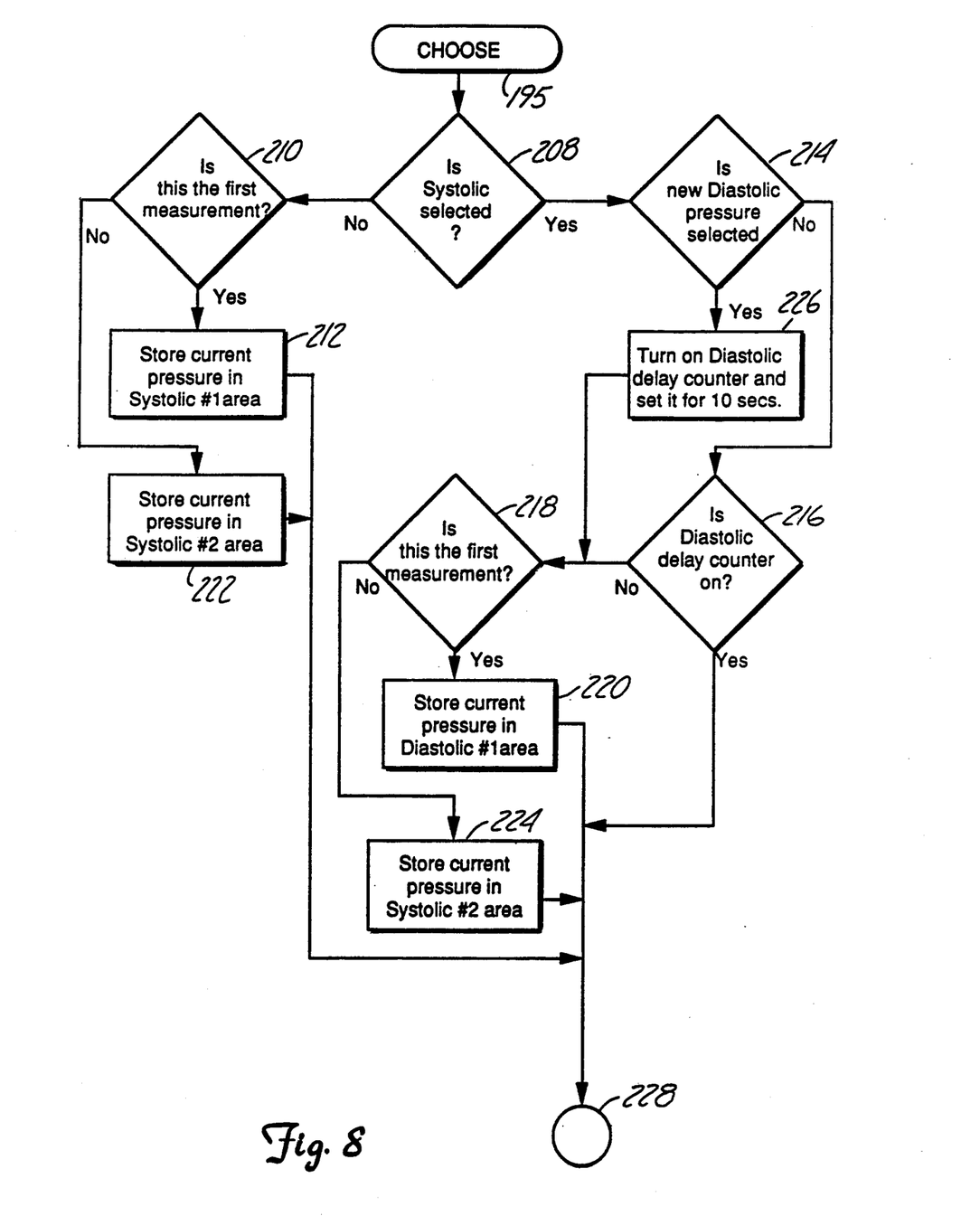

Returning to step 208, a positive response moves program execution to step 214, which is a further decision branch labeled "IS NEW DIASTOLIC PRESSURE SELECTED?". A negative response moves program execution to step 216 which is a further decision branch labeled "IS DIASTOLIC DELAY COUNTER ON?". A negative response moves program execution to step 218, which is a further decision branch labeled "IS THIS THE FIRST MEASUREMENT?". If this is the first measurement, current measured blood pressure is stored in Diastolic area #1 (step 220).

Returning to step 210, if this is not the first measurement, current measured blood pressure is stored in Systolic area #2 (step 222). Returning to step 218, if this is not the first measurement, current measured blood pressure is stored in Diastolic area #2 (step 224). Returning to step 214, a positive response moves program execution to step 226 which turns on the diastolic delay counter and sets it for 10 seconds. Program execution then moves on to step 218.

Figure 9:
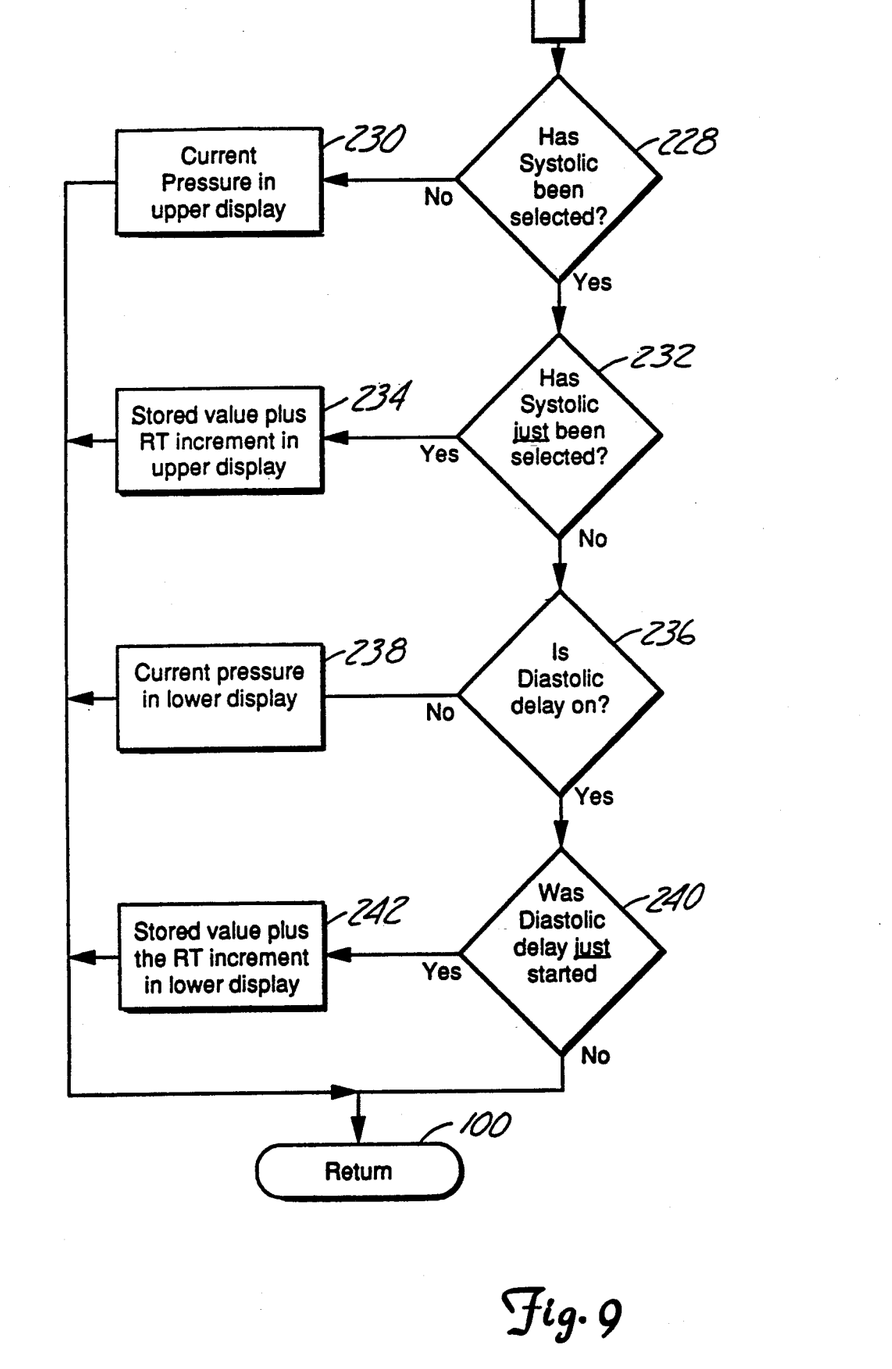

Program execution from any of steps 212, 222, 216, 220 or 224 moves to step 228 (FIG. 9). Step 228 is a decision branch labeled "HAS SYSTOLIC BEEN SELECTED?". A negative response causes the current measured blood pressure to be displayed in display 28 (step 230) and a return to step 100. A positive response at 228 moves program execution to step 232 which is a decision branch labeled "HAS SYSTOLIC JUST BEEN SELECTED?". A positive response causes the stored value plus the RT (i.e. reaction time) pressure increment to be displayed in display 28 (step 234) and a return to step 100. A negative response at 232 moves program execution to step 236 which is a decision branch labeled "IS DIASTOLIC DELAY ON?". A negative response causes the current measured blood pressure to be displayed in display 30 (step 238) and a return to step 100. A positive response at 236 moves program execution to step 240 which is a decision branch labeled "WAS DIASTOLIC DELAY JUST STARTED?". A positive response causes the stored value plus the RT increment to be displayed in display 30 (step 242) and a return to step 100. A negative response at step 240 moves program execution to step 100.

A negative response at step 128 or a positive response at step 142 moves program execution to step 195. Returning to step 102 (FIG. 3), a negative response moves program execution to step 244. If both buttons 32 and 34 are depressed simultaneously, system 26 is turned on (step 246). If both buttons 32 and 34 are not depressed, program execution moves back to step 100 for reentry into the routine operation described.

Although the present invention has been described with reference to preferred embodiments, workers skilled in the art will recognize that changes may be made in form and detail without departing from the spirit and scope of the invention.

What is claimed is:

1. A sphygmomanometer comprising:
   a nonyielding arm cuff;
   an inflatable air bladder in the arm cuff;
   means for inflating the air bladder;
   a pressure transducer connected to the air bladder and having a pressure reading output signal terminal;
   an outlet valve connected to the air bladder;
   means responsive to an electrical signal for controlling the outlet valve;
   manually operated means for generating systolic and diastolic interrupt signals;
   data processing means responsive to the interrupt signals for recording pressure reading output signals; and
   display means for displaying indications of pressure from the pressure reading output signals.

2. A sphygmomanometer as claimed in claim 1 wherein the data processing means includes a microprocessor, the microprocessor providing electrical signals to the means for controlling the outlet valve.

3. A sphygmomanometer as claimed in claim 2 wherein the manually operated means for generating systolic and diastolic signals further includes a control system having a manually actuated systolic observation switch and a manually actuated diastolic observation switch, where closure of either switch generates the interrupt signals applied to the microprocessor.

4. A sphygmomanometer as claimed in claim 1 wherein the means for controlling the outlet valve is a solenoid.

5. A sphygmomanometer as claimed in claim 1 and further comprising a mercury column manometer connected to the air bladder.

6. A sphygmomanometer comprising:
   a nonyielding arm cuff;
   an air bladder retained in the arm cuff;
   means for inflating the air bladder;
   a pressure transducer connected to the air bladder having a pressure signal terminal;
   an outlet valve connected to the air bladder;
   means responsive to an electrical signal for controlling the outlet valve;
   data processing means responsive to interrupts for recording a pressure signal, for generating an electrical signal controlling the outlet valve, for timing out a rest period between first and second blood pressure measurements of a patient, and for generating display control signals;
   manually operated means for generating interrupts; and
   display means responsive to the display control signals for displaying pressure readings.

7. A sphygmomanometer as set forth in claim 6 further comprising a mercury column manometer connected to the air bladder.

* * * * *